United States Patent [19]
Chen et al.

[11] Patent Number: 4,579,123
[45] Date of Patent: Apr. 1, 1986

[54] STAND-OFF DEVICE

[75] Inventors: James N. Chen, Chelmsford; Thaddeus G. Minior, Tewksbury, both of Mass.

[73] Assignee: Hewlett-Packard Company, Palo Alto, Calif.

[21] Appl. No.: 562,124

[22] Filed: Dec. 16, 1983

[51] Int. Cl.[4] .............................................. A61B 10/00
[52] U.S. Cl. .................................... 128/660; 73/644
[58] Field of Search .................... 128/660–663; 73/619–620, 625–626, 642, 644

[56] References Cited

U.S. PATENT DOCUMENTS

| | | | |
|---|---|---|---|
| 3,765,403 | 10/1973 | Brenden | 128/660 |
| 3,964,296 | 6/1976 | Matzuk | 128/660 X |
| 4,059,098 | 11/1977 | Murdock | 128/660 |
| 4,237,901 | 12/1980 | Taenzer | 128/660 |
| 4,316,271 | 2/1982 | Evert | 367/140 |
| 4,333,474 | 6/1982 | Nigam | 128/660 |
| 4,407,293 | 10/1983 | Suarez, Jr. et al. | 128/660 |
| 4,424,813 | 1/1984 | Havlice et al. | 128/660 |
| 4,469,106 | 9/1984 | Harui | 128/660 |

FOREIGN PATENT DOCUMENTS

| | | | |
|---|---|---|---|
| 2604023 | 8/1977 | Fed. Rep. of Germany | 128/660 |
| 2318613 | 2/1977 | France | 128/660 |
| 1432349 | 4/1976 | United Kingdom | 367/166 |

*Primary Examiner*—Kyle L. Howell
*Assistant Examiner*—Francis J. Jaworski
*Attorney, Agent, or Firm*—Donald N. Timbie

[57] ABSTRACT

A stand-off device for use with an acoustic transducer in the form of a volume having a flexible cup section and a stiff cup section with the lips of the cups joined together and almost filled with liquid. The bottom of the stiff cup section has an opening across which a membrane is mounted and a clip for holding the active section of a transducer in contact with the membrane.

7 Claims, 7 Drawing Figures

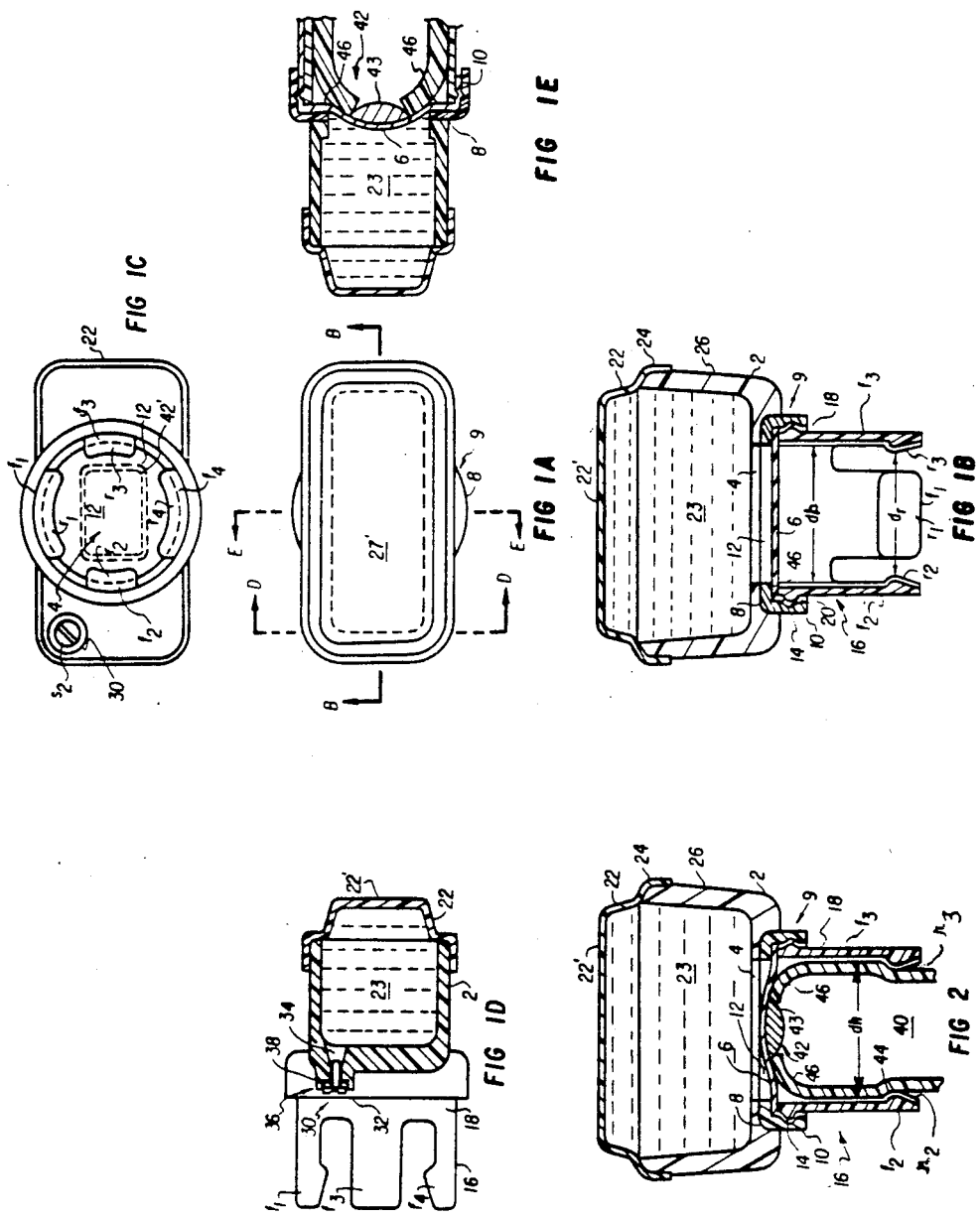

STAND-OFF DEVICE

BACKGROUND OF THE INVENTION

In ultrasonic systems used to image the interior of a patient's body, a transducer transmits acoustic energy into the body and receives echoes from structures therein. It converts the energy in these echoes into electrical signals that are used to form an image. In many cases, structures close to the surface of the body are not in a region of sharp focus because of their proximity to the transducer, but they can be placed farther away from the transducer so as to be in a region of better focus by insertion of a stand-off device between the transducer and the patient's body. A plastic bag filled with liquid may be used for this purpose. Furthermore, in a system producing an image in the form of a sector, it is difficult to identify structures near the apex because of the limited field of view. This problem can also be eliminated by use of a stand-off device because the structures previously at the apex can be placed properly within the sector where more of the surrounding structure is visible.

In some known stand-off devices, the surface of the stand-off device that contacts the body has been made of flexible material, but the volume within the device has been filled with liquid so that pressure must be applied to bring a desired amount of the surface into intimate contact with the patient's body. This causes the relative positions of the structures being observed to be disturbed.

BRIEF DESCRIPTION OF THE INVENTION

A stand-off device constructed in accordance with this invention is comprised of a cup section made of flexible material having its lip joined to the lip of a cup section made of relatively stiff material, enough bubble-free liquid contained in said cup sections to fill the volume of the stiff cup section and partially fill the volume of the flexible cup section, the remainder of the volume being gas-free, and an opening in the bottom of the stiff cup section whereby a transducer may be acoustically coupled to the liquid. When the flexible cup section is lightly pressed against the body of a patient, its geometry is modified to a point where good acoustical coupling is established between the body of the patient and the liquid. The transducer itself may close the opening in the bottom of the stiff cup, or a flexible membrane may be used for this purpose and the transducer mounted in intimate contact therewith. In either case, good acoustical coupling must be provided between the transducer and the liquid. The stand-off device can be separate from the transducer and have means for holding the transducer in its proper position, or it can be an integral part of the transducer.

The stiff cup section generally but not necessarily occupies most of the distance between the transducer and the body of the patient and is strong enough to maintain its shape when the flexible cup section is pressed against the body. Alternatively, the walls of the stiff cup section can be strong enough to retain their general shape and yet flexible enough to permit the depth of the cup section to be changed by squeezing it with the hand.

BRIEF DESCRIPTION OF THE DRAWINGS

FIG. 1A is a view looking down in a flexible cup section of a stand-off device constructed in accordance with this invention;
FIG. 1B is an elevational section BB of FIG. 1A;
FIG. 1C is a bottom view of the stand-off device;
FIG. 1D is the elevational section DD of FIG. 1A;
FIG. 1E is the elevational section EE of FIG. 1A;
FIG. 2 is the elevational section of FIG. 1B with a transducer mounted for operation.

DETAILED DESCRIPTION OF THE INVENTION

Figure 3:
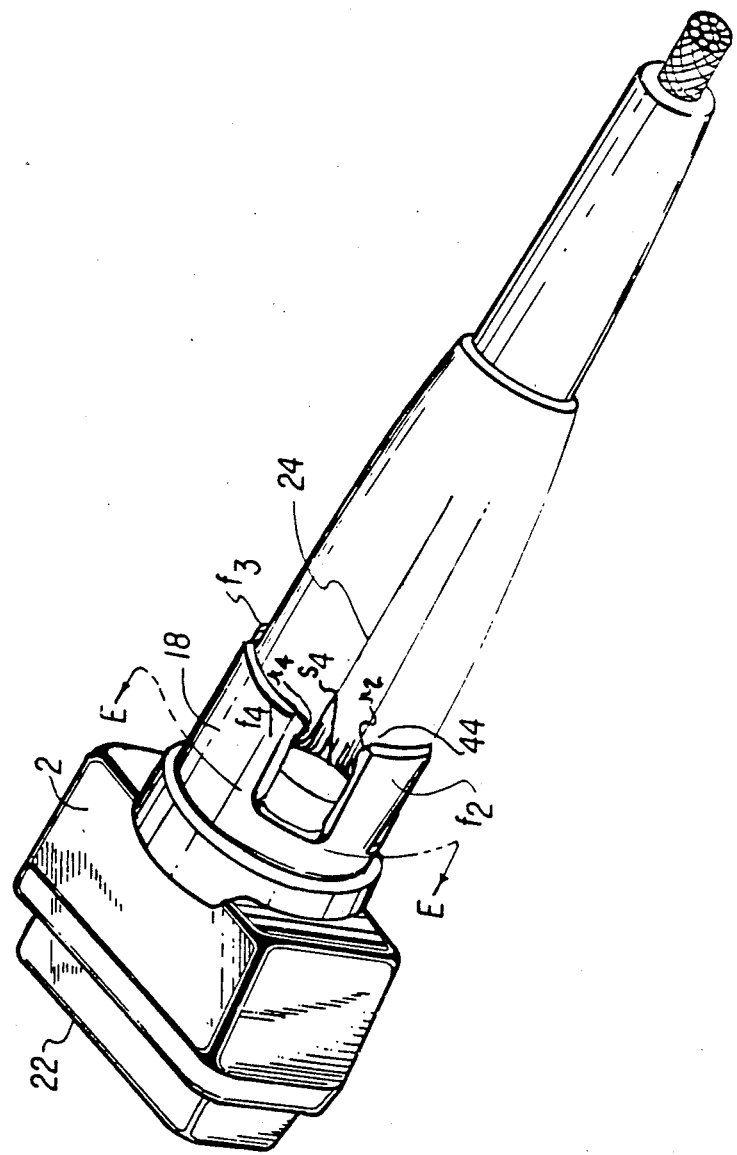
FIG. 3 is an exterior projection view of a stand-off device with a transducer adjoined thereto.

In the following description, corresponding components in the various figures of the drawings are designated in the same way.

Reference is now made to FIG. 1B. A stiff cup section 2 has a rectangular opening 4 formed in its bottom, and a membrane 6 is tautly stretched across the opening 4. In this particular embodiment, a circular top 8 of a cap 9 having a hollow cylindrical skirt 10 extending perpendicularly below its periphery is bonded to a recess in the outer surface of the bottom of the rigid cup 2 with such orientation that a rectangular opening 12 in the top 8 is in registration with the rectangular opening 4. An annular groove 14 on the inner surface of the skirt 10 is located at a given distance from the top 8. A transducer retaining clip 16, which is in the general form of a hollow cylinder, has an annular base 18 and four fingers $f_1$, $f_2$, $f_3$ and $f_4$ extending perpendicularly therefrom, but only fingers $f_1$, $f_2$ and $f_3$ appear in FIG. 1B. The outer diameter of the base 18 is slightly less than the inner diameter of the skirt 10, and an annular ridge 20 is located on the outer surface of the base 18 at a distance from the top of the clip 16 that is slightly less than the distance of the groove 14 from the top 8 of the cap 9. Thus, when the membrane 6 is stretched taut over the base 18 of the clip 16 and down its sides and the clip 16 is inserted into the skirt 10, the ridge 20 engages the groove 14 so as to hold the membrane 6 in position across the bottom of the opening 12 and therefore across the opening 4.

A flexible cup section 22 formed from thin flexible material has a lip 24 cemented to the outer surface of the lip 26 of the rigid cup 2. In order to fit the contours of the body more readily, it is advantageous for the bottom of the flexible cup 22 to be substantially planar.

An important aspect of the invention is the fact that the cups 2 and 22 contain a volume of liquid 23 that is greater than the volume of the cup section 2 and less than the sum of the volume of the cup section 2 and the maximum volume of the cup section 22 at normal ambient conditions. It is important that the liquid 23 contain no air bubbles. With a configuration generally like that shown in the drawings, good results have been attained when the liquid fills 95% of the total cup volumes. In any event, 90% to 98% of the total volume of the cups should be filled.

Introduction of the required amount of liquid into the cup sections 2 and 22 without also introducing air bubbles is made possible by provision of means such as a purging port 30 (FIGS. 1C and 1D) in the bottom of the cup 2. As can be seen in FIG. 1D, which is a vertical section DD of FIG. 1A, the port 30 is comprised of a screw 32 threaded into a passageway 34 that extends entirely through the bottom of the cup 2. The outer end of the passageway 34 has an annular recess 36 which has a diameter slightly larger than the head of the screw 32 and an O-ring 38 mounted in the recess 36 so that when the screw 32 is screwed inwardly, its head squeezes the O-ring 38 so as to form a seal. In order that the cup sections 2 and 22 may contain a desired amount of liquid, the stand-off device is positioned with the axes of the cup sections vertically disposed and the cup section 2 on the bottom. The screw 32 is removed and liquid is poured through the passageway 34 until the cup sections 2 and 22 are filled to overflowing. In this situation, the volume formed by the cup section 22 is a maximum. At this point, the device is lowered onto a flat horizontal surface so as to push the bottom of the flexible cup section 22 upward and cause a desired amount of fluid to overflow from the passageway 34. The screw 32 is then inserted and tightened against the O-ring 38 so as to form a seal. If improper use should cause air bubbles to form in the liquid, the process can be repeated. If this contingency is not provided for, the passageway 34 could be permanently sealed off when the right amount of fluid has overflowed.

If the cup section 2 and the maximum volume of the cup section 22 were entirely filled with liquid, the bottom of the cup section 22 would be curved and would have to be firmly pressed against the body of a patient in order to ensure contact throughout the required surface area even though the cup section 22 is molded with the surface 22' perpendicular to the cup axis being flat. As previously pointed out, such firm pressure would disturb the relative locations of structures in the body. But when the combined volumes of the cup sections 2 and 22 are nearly filled, e.g., 95%, as just described, very little pressure is required to make the bottom 22' of the cup 22 conform to the shape of the body so that the relative positions of structures within the body are not disturbed and the interior of the body can be viewed as it is. More importantly, however, good contact between the bottom 22' of the cup 22 and the body is easily achieved.

It is equally important that the entire active area of a transducer lens be in intimate contact with the outside of the membrane 6. This function is peformed by the clip 16 for a transducer having the shape of the transducer 40 depicted in FIGS. 2 and 3, but it is understood that the design of the clip 16 may be different for transducers having a different shape. The outside of the transducer 40 has a cylindrical cross-section at the point indicated by the arrow dh, FIG. 2, and tapers to a smaller nearly rectangular cross-section as it approaches its active area 42. The area 42 may be covered by a rubber lens 43. Although not shown, the active area 42 has a rectangular configuration that is proportional to the rectangular openings 4 and 12. On the lower side of the arrow dh, the outer diameter of the transducer 40 is reduced so as to form a step 44. The fingers $f_1$ through $f_4$ are respectively provided with ridges $r_1$ through $r_4$ at the outer ends of their inside surfaces, but only the fingers $f_2$ and $f_3$ of the clip 16 appear in FIG. 2. The finger $f_1$ also appears in FIG. 1B. As seen in FIG. 1B, the diameter dr of the circle on which the innermost surfaces of the ridges $r_1$ through $r_4$ lie is less than the internal diameter db of the base 18 of the clip 16. The diameter db is slightly larger than the maximum outer diameter dh of the transducer 40. Thus, as the transducer 40 is being inserted within the fingers $f_1$, $f_2$, $f_3$ and $f_4$, there comes a point when the outer surface of the transducer 40 engages the inner ridges $r_1$, $r_2$, $r_3$ and $r_4$ so as to expand them in a radially outward direction. When the annular step 44 reaches the ridges $r_1$, $r_2$, $r_3$ and $r_4$, the fingers $f_1$, $f_2$, $f_3$ and $f_4$ start to contract; and when the inner end of the transducer reaches a point where it is in contact with the membrane 6 at the corner 46 of the opening 12 in the top 8 of the cap 9, the interior surfaces of the ridges $r_1$, $r_2$, $r_3$ and $r_4$ are in contact with the exterior surface of the step 44. The shape of the step 44 in an axial plane complements the shape of the ridges $r_1$, $r_2$, $r_3$ and $r_4$ so as to provide good contact between them and firmly retain the transducer 40 in position.

It is important to notice that when the transducer 40 is inserted in the clip 16 in the manner just described, its lens 43 presses the diaphragm 6 upward into the opening 12 so as to establish intimate contact between them.

Reference is now made to FIG. 3 for a description of the construction details of the transducer 40 that permit its rectangular active area 42 to be oriented with the rectangular opening 12 in the top 8 of the cap when it is inserted into the clip 16. In FIG. 3, the annular step 44 of FIG. 2 is replaced by four steps $S_1$ through $S_4$ having the same shape in an axial plane as the step 44. Only $S_4$ appears in FIG. 3. When the steps $S_1$ through $S_4$ are oriented so as to be respectively under the fingers $f_1$ through $f_4$, they fit with the ridges $r_1$ through $r_4$ respectively in the same manner as the step 44, and the registration between the active area 42 of the transducer 40 and the rectangular opening 12 is obtained.

It would be possible to remove the transducer 40 from the clip 16 of FIG. 3 by exerting sufficient axial force so that the steps $S_1$ through $S_4$ respectively push the fingers $f_1$ through $f_4$ in a radially outward direction through interaction with the ridges $r_1$ through $r_4$, but this can be done more easily by rotating the transducer 40 to the position shown in FIG. 3 wherein the steps $S_1$ through $S_4$ are between the fingers.

As the transducer 40 is rotated, an outward axial force is applied to it so as to make its removal easier. This action results from the shape of the outer surface of the transducer 40 surrounding the lens 43. The shape is such that the transducer 40 contacts the edge 46 as indicated by a dash-dot line 42' of FIG. 1C. Contact is made at the center of the sides of the opening 12. As seen in FIG. 1E, the transducer 40 is curved in an axial plane passing through the latter points of contact. It is curved in a similar manner in axial planes on either side of the central one shown in FIG. 1C. Therefore, when the transducer 40 is rotated about its longitudinal axis, the surface surrounding the lens 43 rides up on the edge 46 so as to force the transducer in an outward direction.

Although the stand-off device has been shown as being separate from the transducer 40, it could be formed as an integral part thereof, in which event the clip 16 would not be used.

What is claimed is:

1. A stand-off device for insertion between a transducer and the body of a patient, comprising
   a stiff cup section having a lip and a bottom and having a given volume, said bottom having means defining an opening therein,
   means for closing said opening,
   a flexible cup section having a bottom and a lip,
   said lips of said cup sections being joined with said bottoms on opposite sides thereof so as to form a sealed space, said cup sections being so dimensioned that said sealed spaced has a maximum volume under the ambient condition of use equal to the volume of liquid it contains when filled to overflowing with said flexible cup section below said stiff cup section, and said sealed space having inserted therein only a volume of liquid equal to a fraction of said maximum volume and greater than the given volume of said stiff cup section.

2. A stand-off device as set forth in claim 1 wherein said fraction is between 90% and 98% inclusive.

3. A stand-off device as set forth in claim 1 in which a closeable air purging port is mounted in the bottom of said stiff cup-like section.

4. A stand-off device as set forth in claim 1 wherein said means for closing said opening is a membrane.

5. A stand-off device as set forth in claim 1 wherein said means for closing said opening is a transducer.

6. A stand-off device as set forth in claim 1 wherein said flexible cup section is made of plastic material.

7. A stand-off device as set forth in claim 1 wherein said flexible cup section is made of plastic.

* * * * *